(12) United States Patent
Sgroi, Jr. et al.

(10) Patent No.: US 11,160,556 B2
(45) Date of Patent: Nov. 2, 2021

(54) THREADED TROCAR FOR ADAPTER ASSEMBLIES

(71) Applicant: Covidien LP, Mansfield, MA (US)

(72) Inventors: Anthony Sgroi, Jr., Wallingford, CT (US); Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 309 days.

(21) Appl. No.: 16/351,789

(22) Filed: Mar. 13, 2019

(65) Prior Publication Data

US 2019/0321045 A1 Oct. 24, 2019

Related U.S. Application Data

(60) Provisional application No. 62/661,266, filed on Apr. 23, 2018.

(51) Int. Cl.
*A61B 17/115* (2006.01)
*A61B 17/34* (2006.01)
*A61B 17/00* (2006.01)

(52) U.S. Cl.
CPC ....... *A61B 17/1155* (2013.01); *A61B 17/3417* (2013.01); *A61B 2017/00473* (2013.01); *A61B 2017/3454* (2013.01)

(58) Field of Classification Search
None
See application file for complete search history.

(56) References Cited

U.S. PATENT DOCUMENTS

| | | | |
|---|---|---|---|
| 2,777,340 A | 1/1957 | Hettwer et al. |
| 2,957,353 A | 10/1960 | Babacz |
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |

(Continued)

FOREIGN PATENT DOCUMENTS

| | | |
|---|---|---|
| CA | 2451558 A1 | 1/2003 |
| CN | 1547454 A | 11/2004 |

(Continued)

OTHER PUBLICATIONS

European Search Report dated Sep. 10, 2019, issued in EP Appln. No. 19170304.

(Continued)

*Primary Examiner* — Anna K Kinsaul
*Assistant Examiner* — Chinyere J Rushing-Tucker
(74) *Attorney, Agent, or Firm* — Carter, DeLuca & Farrell LLP

(57) ABSTRACT

A trocar assembly for releasable engagement with an adapter assembly of a surgical stapling instrument includes a housing having a first end cap and a second end cap, a trocar member rotatably supported with the housing and movable between a retracted position and an advanced position, and a drive member rotatably supported within the housing. The trocar member includes a threaded body and defines a longitudinal channel. The drive member includes a drive portion received within the longitudinal channel of the trocar member. Rotation of the drive member causes longitudinal movement of the trocar member.

19 Claims, 5 Drawing Sheets

(56) References Cited

U.S. PATENT DOCUMENTS

| | | |
|---|---|---|
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |

(56) References Cited

U.S. PATENT DOCUMENTS

| | | |
|---|---|---|
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0027469 A1 | 2/2007 | Smith et al. |
| 2007/0029363 A1 | 2/2007 | Popov |
| 2007/0084897 A1 | 4/2007 | Shelton et al. |

(56) References Cited

U.S. PATENT DOCUMENTS

| | | |
|---|---|---|
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1* | 4/2016 | Cabrera ............ A61B 17/1155 606/1 |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 1957854 A | 5/2007 |
| CN | 101495046 A | 7/2009 |
| CN | 102247182 A | 11/2011 |
| DE | 102008053842 A1 | 5/2010 |
| EP | 0705571 A1 | 4/1996 |
| EP | 1563793 A1 | 8/2005 |
| EP | 1769754 A1 | 4/2007 |
| EP | 2316345 A1 | 5/2011 |
| EP | 2668910 A2 | 12/2013 |
| EP | 3205288 A1 | 8/2017 |
| ES | 2333509 A1 | 2/2010 |
| JP | 2005125075 A | 5/2005 |
| KR | 20120022521 A | 3/2012 |
| WO | 2011108840 A2 | 9/2011 |
| WO | 2012/040984 A1 | 4/2012 |

(56) References Cited

FOREIGN PATENT DOCUMENTS

| | | |
|---|---|---|
| WO | 2014099704 A2 | 6/2014 |
| WO | 2017172900 A1 | 10/2017 |

OTHER PUBLICATIONS

Extended European Search Report corresponding to International Application No. EP 14 18 4882.0 dated May 12, 2015.
Canadian Office Action corresponding to International Application No. CA 2640399 dated May 7, 2015.
Japanese Office Action corresponding to International Application No. JP 2011-197365 dated Mar. 23, 2015.
Japanese Office Action corresponding to International Application No. JP 2011-084092 dated May 20, 2015.
Japanese Office Action corresponding to International Application No. JP 2014-148482 dated Jun. 2, 2015.
Extended European Search Report corresponding to International Application No. EP 14 18 9358.6 dated Jul. 8, 2015.
Extended European Search Report corresponding to International Application No. EP 14 19 6148.2 dated Apr. 23, 2015.
Partial European Search Report corresponding to International Application No. EP 14 19 6704.2 dated May 11, 2015.
Australian Office Action corresponding to International Application No. AU 2010241367 dated Aug. 20, 2015.
Partial European Search Report corresponding to International Application No. EP 14 19 9783.3 dated Sep. 3, 2015.
Extended European Search Report corresponding to International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
European Search Report EP 15 156 035.6 dated Aug. 10, 2016.
European Search Report corresponding to EP 15 184 915.5-1654 dated Sep. 16, 2016.
Australian Examination Report No. 1 corresponding to International Application No. AU 2013205872 dated Oct. 19, 2016.
Australian Examination Report from Appl. No. AU 2013205840 dated Nov. 3, 2016.

\* cited by examiner

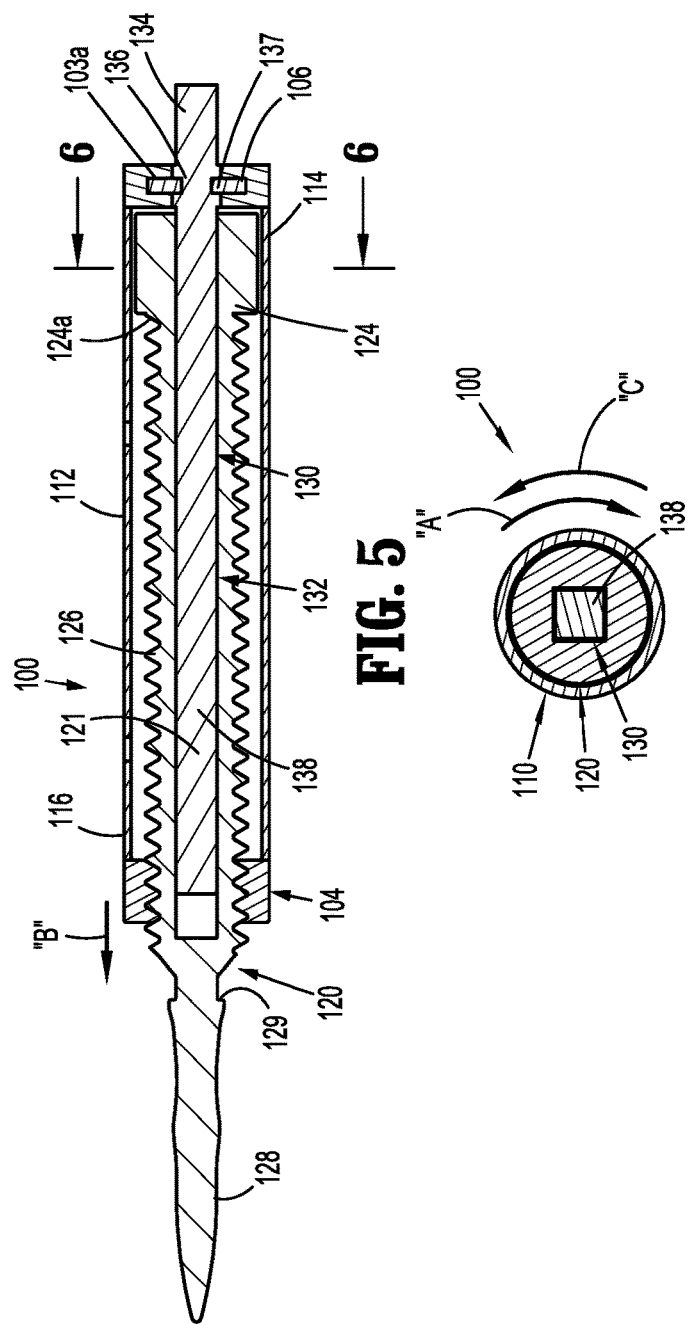
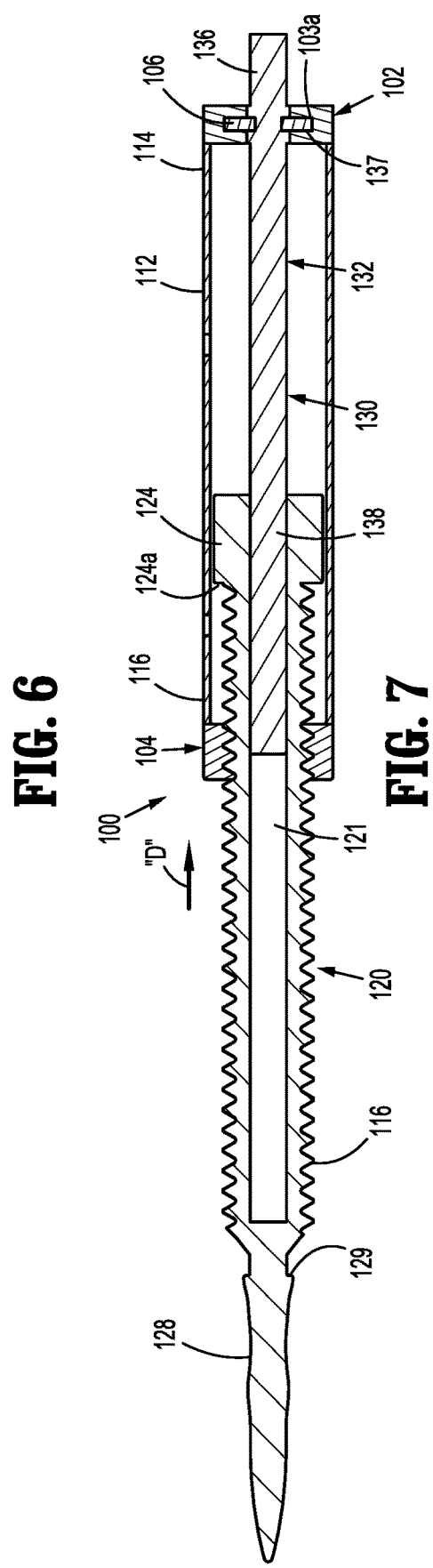

THREADED TROCAR FOR ADAPTER ASSEMBLIES

CROSS-REFERENCE TO RELATED APPLICATIONS

This application claims the benefit of and priority to U.S. Provisional Patent Application Ser. No. 62/661,266 filed Apr. 23, 2018, the entire disclosure of which is incorporated by reference herein.

BACKGROUND

Technical Field

The present disclosure relates to circular stapling instruments. More particularly, the present disclosure relates to threaded trocars for use in adapter assemblies for circular stapling instruments.

Background of Related Art

Surgical instruments for applying staples, clips, or other fasteners to tissue are well known. Typically, endoscopic stapling instruments include an actuation unit, i.e., a handle assembly for actuating the instrument, an elongate shaft for accessing a body cavity, and a tool assembly disposed at a distal end of the elongate shaft.

Adapter assemblies used with a circular stapling tool assembly include a trocar assembly for selectively positioning an anvil assembly relative to a cartridge assembly. To facilitate sterilization and reuse of the adapter assemblies, many adapter assemblies include a removable trocar assembly.

SUMMARY

A trocar assembly for releasable engagement with an adapter assembly of a surgical stapling instrument is provided. The trocar assembly includes a housing having a first end cap and a second end cap, a trocar member rotatably supported with the housing and movable between a retracted position and an advanced position, and a drive member rotatably supported within the housing. The trocar member includes a threaded body and defines a longitudinal channel. The drive member includes a drive portion received within the longitudinal channel of the trocar member. Rotation of the drive member causes longitudinal movement of the trocar member.

In embodiments, the second end cap includes a threaded bore. The threaded body of the trocar member may be received through the threaded bore of the second end cap to cause the longitudinal movement of the trocar member during rotation of the drive member. The first end cap may include a bore and the drive member may include an engagement portion received through the bore. The drive member and the trocar member may be longitudinally fixed relative to each other. Rotation of the drive member in a first direction may cause rotation advancement of the trocar member. Rotation of the drive member in a second direction may cause retraction of the trocar member.

In some embodiments, the second end cap is configured to retain the trocar member within the housing. The housing may define at least one slot for facilitating attachment of the trocar assembly within an adapter assembly. A distal end of the trocar member may be configured for operable engagement by an anvil assembly. The distal end of the trocar member may include a tapered end.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein:

FIG. 5 is a cross-sectional side view of the trocar assembly shown in FIG. 3, with a trocar member in a retracted position;

FIG. 6 is a cross-sectional end view taken along line 6-6 shown in FIG. 5; and

FIG. 7 is a cross-sectional side view of the trocar assembly shown in FIG. 3, with a trocar member in an advanced position.

DETAILED DESCRIPTION

Figure 1:
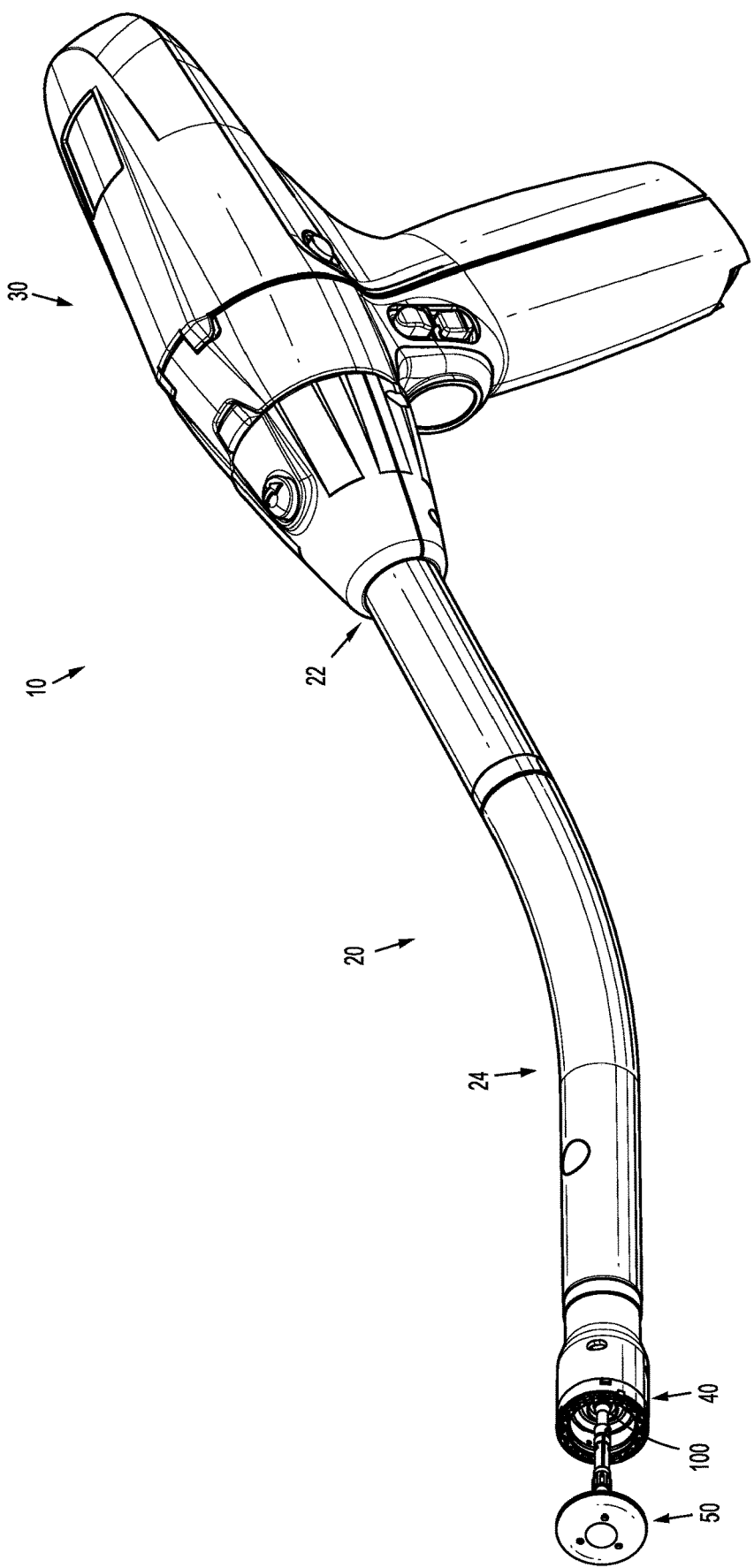
FIG. 1 is a perspective view of a surgical stapling instrument including trocar assembly according to an embodiment of the present disclosure.

Embodiments of the presently disclosed removable trocar assembly will now be described in detail with reference to the drawings in which like reference numerals designate identical or corresponding elements in each of the several views. As is common in the art, the term "proximal" refers to that part or component closer to the user or operator, i.e. surgeon or clinician, while the term "distal" refers to that part or component farther away from the user.

Referring initially to FIG. 1, an adapter assembly suitable for use with a removable trocar assembly according to an embodiment of the present disclosure, shown generally as adapter assembly 20, is a component of a surgical stapling instrument 10. The surgical stapling instrument 10 further includes a powered handle assembly 30, a loading unit 40, and an anvil assembly 50. Although shown and described with reference to surgical stapling instrument 10, the aspects of the present disclosure may be modified for use with surgical stapling instruments having alternative configurations. For a detailed description of exemplary powered surgical stapling instruments, please refer to commonly owned U.S. Pat. No. 9,023,014 ("the '014 patent) and U.S. Pat. No. 9,055,943 ("the '943 patent"), the contents of which are incorporated by reference herein in their entirety.

The adapter assembly 20 of the surgical stapling instrument 10 will only be described to the extent necessary to fully disclose the aspects of the present disclosure. For a detailed description of exemplary adapter assemblies, please refer to commonly owned U.S. Pat. App. Pub. Nos. 2016/0106406 ("the '406 publication) and 2017/0086879 ("the '879 publication"), the contents of which are incorporated by reference herein in their entirety.

Figure 2:
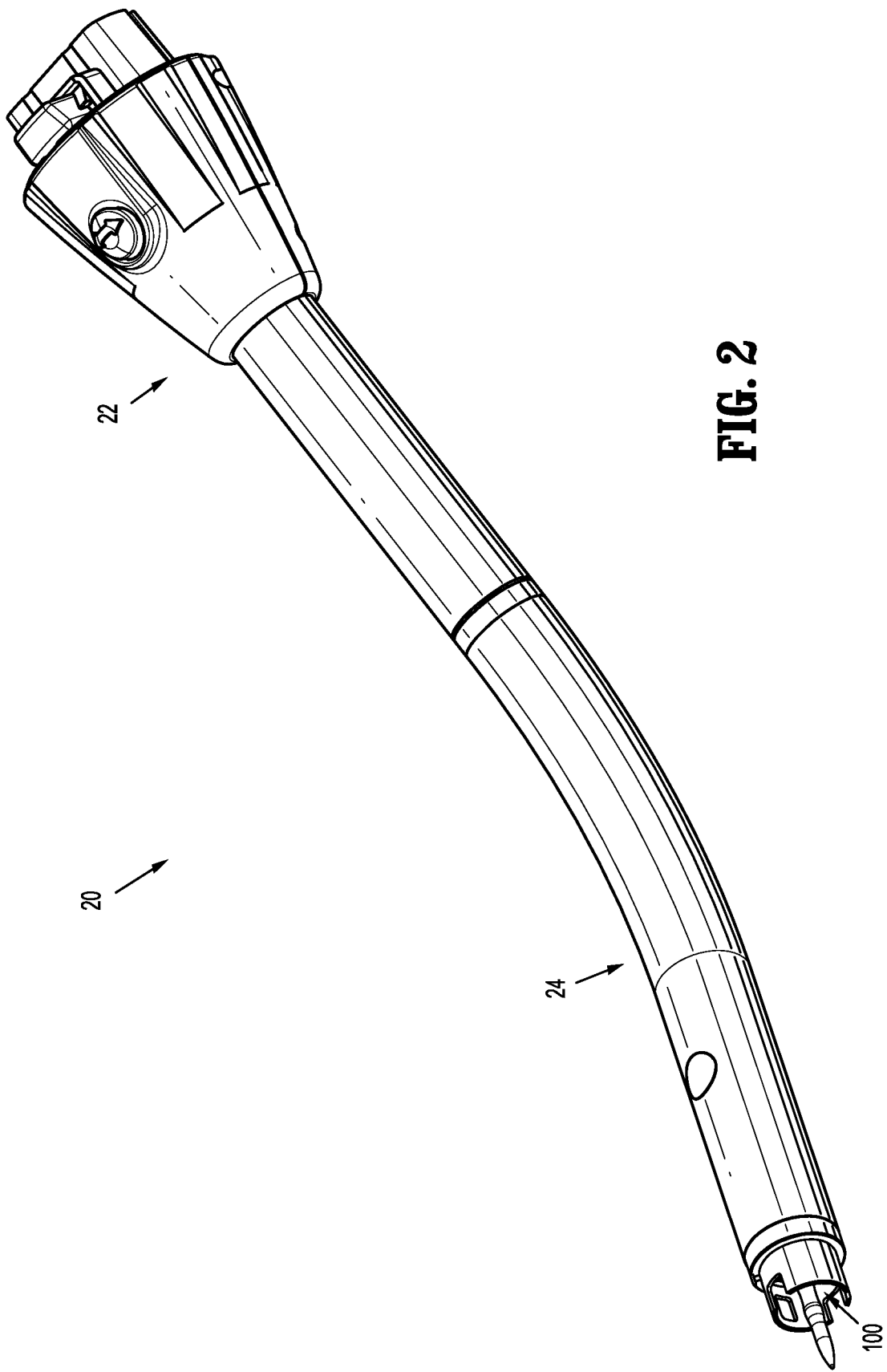
FIG. 2 is a perspective view of an adapter assembly of the surgical stapling instrument shown in FIG. 1.

With reference to FIG. 2, the adapter assembly 20 includes a proximal portion 22 configured for operable connection to the handle assembly 30 (FIG. 1) and a distal portion 24 configured for operable connection to the loading unit 40 (FIG. 1). Although shown and described as forming an integral unit, it is envisioned that the proximal and distal portions 22, 24 may be formed as separate units that are releasably securable to one another.

Figure 3:
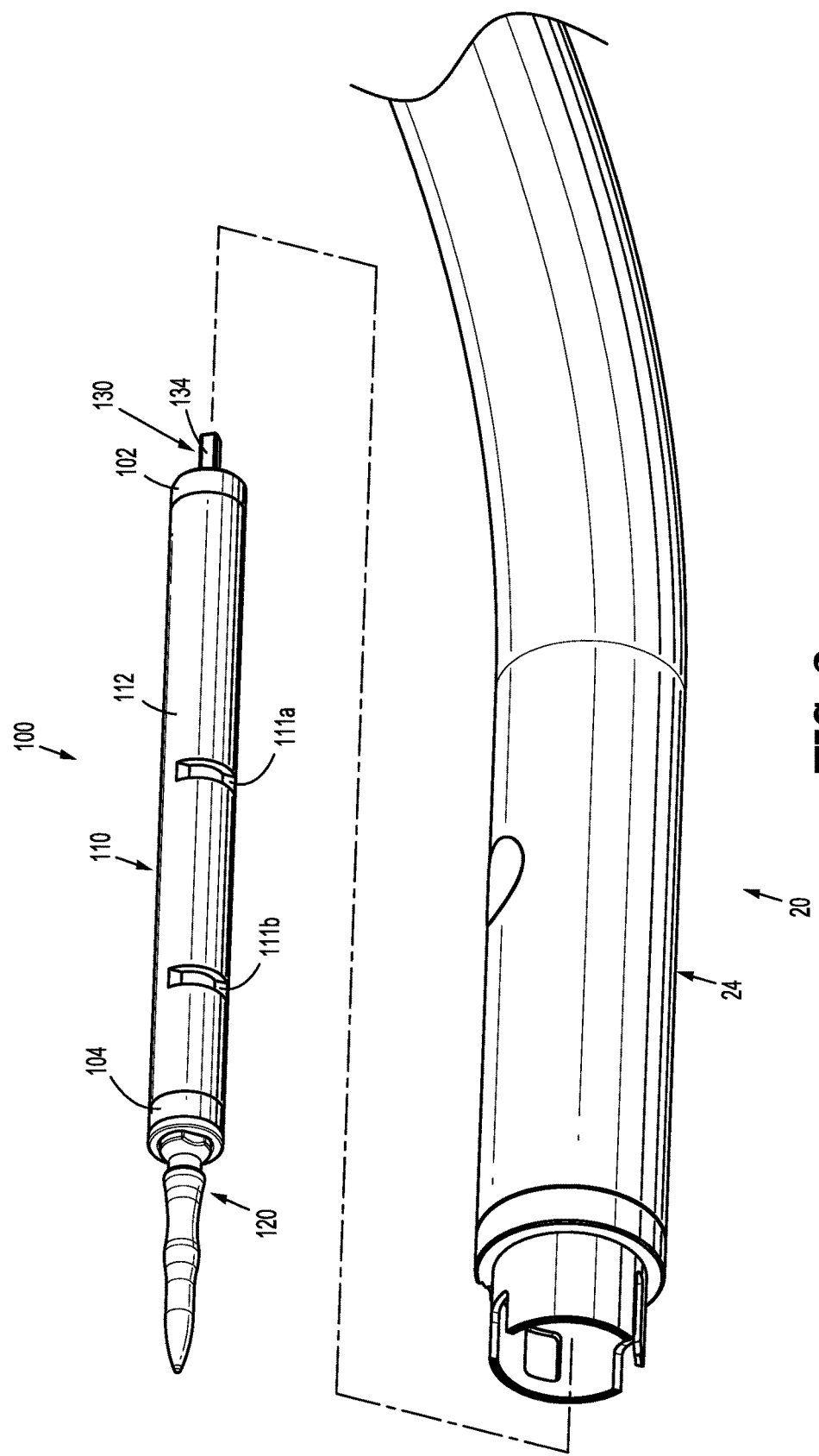
FIG. 3 is a perspective view of a proximal portion of the adapter assembly shown in FIG. 1 and a trocar assembly according to an embodiment of the present disclosure.

Turning to FIG. 3, the removable trocar assembly according to an embodiment of the present disclosure, shown generally as trocar assembly 100, extends distally from the distal portion 24 of the adapter assembly 20 of the surgical stapling instrument 10. The trocar assembly 100 is releasably secured within the distal portion 24 of the adapter assembly 20. For a detailed description of an exemplary locking mechanism for securing the trocar assembly 100 within the distal portion 24 of the adapter assembly 20, please refer to the '879 publication, the content of which was previously incorporated by reference herein.

Figure 4:
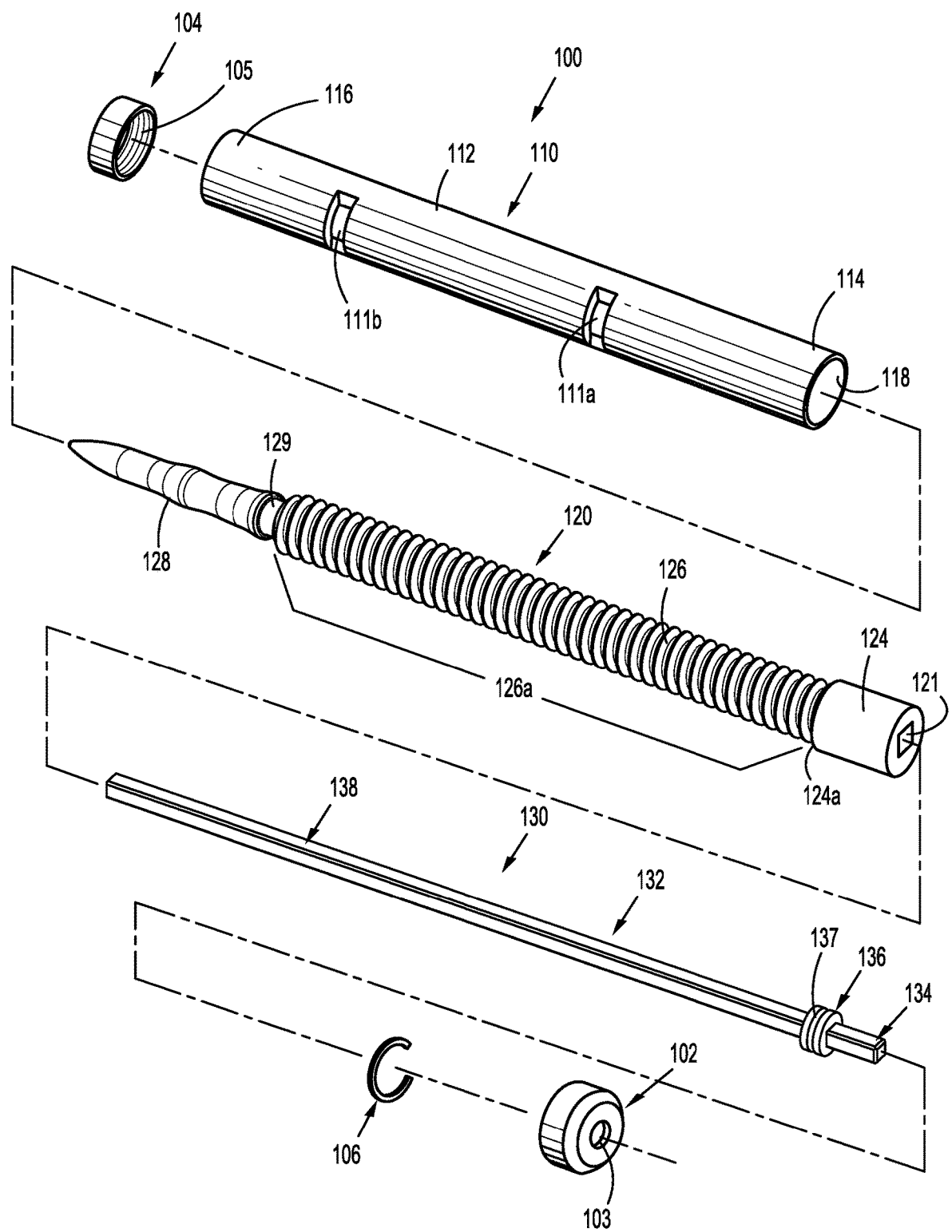
FIG. 4 is a perspective view of the trocar assembly shown in FIG. 3, with components separated.

With particular reference now to FIG. 4-6, the trocar assembly 100 of the adapter assembly 100 (FIG. 2) of the surgical stapling instrument 10 includes a housing 110, a trocar member 120 rotatably disposed within the housing 110, and a drive member 130 received within the trocar member 120 for rotating the trocar member 120 relative to the housing 110. As will be described in further detail below, the trocar member 120 and the drive member 130 are operably retained within the housing 110 by proximal and distal end caps 102, 104. By limiting the number of components of the trocar assembly 100, the cost of manufacturing the trocar assembly 100 is reduced.

The housing 110 of the trocar assembly 100 includes a substantially tubular body 112 having proximal and distal portions 114, 116. In embodiments, the tubular body 112 defines a pair of slots 111a, 111b to facilitate releasable attachment of the trocar assembly 100 within the distal portion 24 of the adapter assembly 20 of the surgical stapling instrument 10. Alternatively, the tubular body 112 of the housing 110 may include tabs, slots and tabs, threading, or other suitable configuration for releasable attachment of the trocar assembly 100 to the adapter assembly 20. An inner surface 118 of the housing 110 may include a friction reducing coating or be otherwise configured to facilitate rotational and/or longitudinal movement of the trocar member 120 within the housing 110.

The first and second end caps 102, 104 of the trocar assembly 100 are secured to the proximal and distal portions 114, 116, respectively, of the tubular body 112 of the housing 110. The first and second end caps 102, 104 may be secured to the tubular body 112 using adhesive, welding, friction fit, mechanical interface, e.g., threads or bayonet coupling, or in any other suitable manner.

The first end cap 102 of the trocar assembly 100 defines an opening 103 configured to receive a proximal portion 134 of the drive member 130 therethrough. The first end cap 102 further defines a recess 103a (FIG. 5) for receiving a snap ring 106. The snap ring 106 longitudinally fixes the drive member 130 relative to the housing 110 while permitting rotation of the drive member 130 relative to the housing 110. The end cap 102 may be configured to support a bearing assembly (not shown) for reducing friction between the drive member 130 and the housing 110 and for facilitating rotation of the drive member 130.

The second end cap 104 of the trocar assembly 100 defines a threaded bore 105 configured for threaded engagement with the trocar member 120 of the trocar assembly 100. In embodiments, the second end cap 104 is formed of plastic such as PEEK or other friction reducing material, and/or includes a friction reducing insert or coating to facilitate threaded engagement with the trocar member 120. In other embodiments, second cap 104 is formed in stainless steel and can utilize any desired thread form. In one example, the thread form can utilize acme threads. In another example, the thread form can utilize V-Style threads. In still other examples, the thread form can be a combination of Acme and V-Style. Those having skill in the art can appreciate that second cap 104 can find use with a plurality of materials, utilize a variety of coatings, and have any style thread form.

With continued reference to FIGS. 4-6, the trocar member 120 of the trocar assembly 100 includes an elongate body 122 having a cylindrical proximal portion 124, a threaded central portion 126, and a tapered distal portion 128. The trocar member 120 of the trocar assembly 100 is configured for rotational and longitudinal movement relative to the housing 110 of the trocar assembly 100.

As will be described in further detail below, rotation of the drive member 130 of the trocar assembly 100 in a first rotational direction, i.e., clockwise, as indicated by arrow "A" in FIG. 6, causes rotation of the trocar member 120 in the first rotational direction. Rotation of the trocar member 120 in the first direction causes longitudinal movement of the trocar member 120 in a first longitudinal direction, i.e., advancement, as indicated by arrow "B" in FIG. 5. Conversely, rotation of the drive member 130 of the trocar assembly 100 in a second rotational direction, i.e., counter-clockwise, as indicated by arrow "C" in FIG. 6, causes rotation of the trocar member 120 in the second rotational direction. Rotation of the trocar member 120 in the second rotational direction causes longitudinal movement of the trocar member 120 in a second longitudinal direction, i.e., retraction, as indicated by arrow "D" in FIG. 7.

The cylindrical proximal portion 124 of the trocar member 120 maintains the trocar member 120 in axial alignment with the housing 110 of the trocar assembly 100. The cylindrical proximal portion 124 may include a friction reducing coating or be otherwise configured to facilitate rotational and longitudinal movement of the trocar member 120 relative to the housing 110 of the trocar assembly 100. The cylindrical proximal portion 124 of the trocar member 120 also acts as a stop member for retaining the trocar member 120 within the housing 110 of the trocar assembly 100. More particularly, a distal portion 124a of the cylindrical proximal portion 124 of the trocar member 120 engages the second end cap 104 to prevent the trocar member 130 exiting the housing 110 of the trocar assembly 100 during advancement of the trocar member 120.

The threaded central portion 126 of the trocar member 120 of the trocar assembly 100 includes threads 126a that engage the threaded bore 105 of the second end cap 104. The threads 126a are configured such that rotation of the trocar member 120 in the first rotational direction, as indicated by arrow "A" in FIG. 6, moves the trocar member 120 in the first longitudinal direction, as indicated by arrow "B" in FIG. 5, and rotation of the trocar member 120 in the second rotational direction, as indicated by arrow "C" in FIG. 6, moves the trocar member 120 in the second longitudinal direction, as indicated by arrow "D" in FIG. 7.

The tapered distal portion 128 of the trocar member 120 is configured for releasable connection by the anvil assembly 50 of the surgical stapling instrument 10. The tapered distal portion 128 of the trocar member 120 may be configured to pierce or otherwise be received through tissue. The tapered distal portion 128 of the trocar member 120 defines a notch 129 configured to facilitate attachment with the anvil assembly 50.

The elongate body 122 of the trocar member 120 defines a longitudinal channel 121 dimensioned to receive the drive member 130 of the trocar assembly 100. In embodiments, and as shown in FIG. 6, the longitudinal channel 121 includes a square cross-section. It is envisioned that the longitudinal channel 121 may include a cross-section of any shape suitable for fixed rotational engagement with the drive member 130 of the trocar assembly 100. The trocar member 120 include a friction reducing member along the longitudinal channel 121 configured to facilitate longitudinal movement of the trocar member 120 relative to the drive member 130.

Still referring to FIGS. 4-6, the drive member 130 of the trocar assembly 100 includes an elongate body 132 having a proximal engagement portion 134, a bearing portion 136, and a distal drive portion 138. The proximal engagement portion 134 of the drive member 130 is configured for operable engagement with a drive element (not shown) of the handle assembly 30. The bearing portion 136 of the drive member 130 defines a groove 137 configured to receive the snap ring 106 of the trocar assembly 100. The snap ring 106 maintains the drive member 130 longitudinally disposed within the housing 110 of the trocar assembly 100 while permitting rotation of the drive member 130 relative to the housing 110. The drive portion 138 of the drive member 130 is configured to be received within the longitudinal channel 121 of the elongate body 122 of the trocar member 120 of the trocar assembly 100. As noted above, in embodiments, and as shown, the drive portion 138 of the drive member 130 includes a square cross-section corresponding to the square cross-section of the longitudinal channel 121, although other shapes are envisioned. The drive portion 138 may be formed of or include a friction reducing material to permit longitudinal movement of the trocar member 120 relative to the drive member 130.

Operation of the surgical stapling instrument 10, including trocar assembly 100, is substantially similar to the operation of the surgical stapling instrument and trocar assembly shown in and described in the '879 publication.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A trocar assembly for releasable engagement with an adapter assembly of a surgical stapling instrument, the trocar assembly comprising:
    a housing including a first end cap and a second end cap;
    a trocar member rotatably supported with the housing and movable between a retracted position and an advanced position, the trocar member including a threaded body and defining a longitudinal channel; and
    a drive member rotatably supported within the housing and including a drive portion received within the longitudinal channel of the trocar member, wherein the drive member and the trocar member are rotationally fixed relative to each other and rotation of the drive member causes longitudinal movement of the trocar member.

2. The trocar assembly of claim 1, wherein the second end cap includes a threaded bore, the threaded body of the trocar member being received through the threaded bore to cause the longitudinal movement of the trocar member during rotation of the drive member.

3. The trocar assembly of claim 1, wherein the first end cap includes a bore and the drive member includes an engagement portion received through the bore.

4. The trocar assembly of claim 1, wherein rotation of the drive member in a first direction causes rotational advancement of the trocar member.

5. The trocar assembly of claim 4, wherein rotation of the drive member in a second direction causes retraction of the trocar member.

6. The trocar assembly of claim 1, wherein the second end cap is configured to retain the trocar member within the housing.

7. The trocar assembly of claim 1, wherein the housing defines at least one slot for facilitating attachment of the trocar assembly within an adapter assembly.

8. The trocar assembly of claim 1, wherein a distal end of the trocar member is configured for operable engagement by an anvil assembly.

9. The trocar assembly of claim 8, wherein the distal end of the trocar member includes a tapered end.

10. A trocar assembly for releasable engagement with an adapter assembly of a surgical stapling instrument, the trocar assembly comprising:
    a housing;
    a trocar member rotatably supported with the housing and movable between a retracted position and an advanced position, the trocar member including an externally threaded body and defining a longitudinal channel; and
    a drive member rotatably supported within the housing and including a drive portion received within the longitudinal channel of the trocar member, wherein rotation of the drive member causes longitudinal movement of the trocar member.

11. The trocar assembly of claim 10, wherein a distal end of the trocar member is configured for operable engagement by an anvil assembly.

12. The trocar assembly of claim 10, wherein the housing includes an end cap having a threaded bore, the externally threaded body of the trocar member being received through the threaded bore to cause the longitudinal movement of the trocar member during rotation of the drive member.

13. The trocar assembly of claim 12, wherein rotation of the drive member in a first direction causes rotational advancement of the trocar member.

14. The trocar assembly of claim 13, wherein rotation of the drive member in a second direction causes retraction of the trocar member.

15. A trocar assembly for releasable engagement with an adapter assembly of a surgical stapling instrument, the trocar assembly comprising:
    a housing;
    a trocar member rotatably supported with the housing and movable between a retracted position and an advanced position; and
    a drive member rotatably supported within the housing and including a drive portion received within a longitudinal channel of the trocar member, wherein the drive member and the trocar member are rotationally fixed relative to each other and rotation of the drive member causes longitudinal movement of the trocar member.

16. The trocar assembly of claim 15, wherein rotation of the drive member in a first direction causes rotational advancement of the trocar member.

17. The trocar assembly of claim 16, wherein rotation of the drive member in a second direction causes retraction of the trocar member.

18. The trocar assembly of claim 15, wherein the housing includes an end cap having a threaded bore, the externally threaded body of the trocar member being received through the threaded bore to cause the longitudinal movement of the trocar member during rotation of the drive member.

19. The trocar assembly of claim 15, wherein a distal end of the trocar member is configured for operable engagement by an anvil assembly.

\* \* \* \* \*